(12) United States Patent
Suess

(10) Patent No.: US 9,681,834 B2
(45) Date of Patent: Jun. 20, 2017

(54) FINGER GUIDE FOR TESTING BLOOD GLUCOSE AND ASSOCIATED METHODS

(71) Applicant: Carolyn Consulting, LLC, Fletcher, NC (US)

(72) Inventor: Marcus Suess, Asheville, NC (US)

(73) Assignee: Carolyn Consulting, LLC, Fletcher, NC (US)

( * ) Notice: Subject to any disclaimer, the term of this patent is extended or adjusted under 35 U.S.C. 154(b) by 586 days.

(21) Appl. No.: 14/195,238

(22) Filed: Mar. 3, 2014

(65) Prior Publication Data

US 2014/0257066 A1    Sep. 11, 2014

Related U.S. Application Data

(60) Provisional application No. 61/772,705, filed on Mar. 5, 2013.

(51) Int. Cl.
  *G01N 33/50* (2006.01)
  *A61B 5/15* (2006.01)
  *A61B 5/145* (2006.01)
  *A61B 5/157* (2006.01)

(52) U.S. Cl.
  CPC .... *A61B 5/150748* (2013.01); *A61B 5/14532* (2013.01); *A61B 5/157* (2013.01); *A61B 5/150022* (2013.01); *A61B 5/150305* (2013.01); *A61B 5/150358* (2013.01); *A61B 5/150412* (2013.01); *A61B 5/150267* (2013.01)

(58) Field of Classification Search
  None
  See application file for complete search history.

(56) References Cited

U.S. PATENT DOCUMENTS

| 5,077,476 A * | 12/1991 | Rosenthal | A61B 5/14532 250/339.04 |
| 5,511,546 A * | 4/1996 | Hon | A61B 5/02444 600/310 |
| 2004/0267229 A1 | 12/2004 | Moerman et al. | |
| 2013/0253287 A1 * | 9/2013 | Tsai | A61B 5/150748 600/309 |

\* cited by examiner

*Primary Examiner* — Jill Warden
*Assistant Examiner* — Brittany Fisher
(74) *Attorney, Agent, or Firm* — Nexsen Pruet, PLLC; E. Eric Mills

(57) ABSTRACT

A finger guide for testing blood glucose and associated methods are disclosed. More particularly, a blood glucose testing system is provided that includes a finger guide that is wearable by the subject of the blood glucose test and a glucose meter that is retrofitted with a glucose meter coupler. A method of operating the blood glucose testing system includes the steps of guiding a lancing device to a spot on the subject's finger for producing a blood droplet and guiding a test strip in the glucose meter to the same spot on the subject's finger for testing the blood sample.

18 Claims, 15 Drawing Sheets

FINGER GUIDE FOR TESTING BLOOD GLUCOSE AND ASSOCIATED METHODS

CROSS-REFERENCE TO RELATED APPLICATIONS

The presently disclosed subject matter claims priority and is related to U.S. Provisional Patent Application No. 61/772,705, entitled "Finger Guide for Testing Blood Glucose and Associated Methods," filed on Mar. 5, 2013; the entire disclosure of which is incorporated herein by reference.

TECHNICAL FIELD

The presently disclosed subject matter relates generally to mechanisms for testing blood glucose levels and more particularly to a finger guide system for testing blood glucose and associated methods.

BACKGROUND

A blood glucose test measures the amount of a certain type of sugar, called glucose, in a person's blood. The test can be done at home or anywhere using a small portable device called a blood glucose meter. Testing blood sugar at home is often called home blood sugar monitoring or self-testing. The traditional method of testing blood sugar involves pricking the person's finger with a lancing device (or lancet—a small, sharp needle) to produce a blood droplet, putting the blood droplet on a test strip, and/or then placing the test strip into a glucose meter that displays the person's blood sugar level.

For many people the steps of performing the blood glucose test are seemingly simple. For others, however, this process can be difficult or, at best, challenging. For example, individuals with visual impairment, neurological disorders, and/or tremors may have difficulty using the glucose lancing device and properly placing the blood sample at the correct area on the test strip for accurate blood glucose testing. Accordingly, an apparatus and method for performing these required blood tests is needed that mitigates one or more of the difficulties discussed above.

SUMMARY

In one embodiment, a blood glucose testing system is provided. The blood glucose testing system may include a finger guide and a glucose meter coupler. In some embodiments, the finger guide may include a finger guide body, a finger guide sleeve, and a finger guide opening within the finger guide sleeve. Additionally, the glucose meter coupler may include a locking mechanism configured to attach the glucose meter coupler to a glucose meter. In some embodiments, the glucose meter coupler may also include a battery cover portion configured to replace the battery cover of a glucose meter and, using the locking mechanism, couple to the glucose meter in the same manner as the battery cover.

The glucose meter coupler may also include a coupling feature configured to mate with the finger guide opening of the finger guide sleeve. In some embodiments, an opening is provided in the coupling feature to allow a test strip to pass from a test strip receptacle on the glucose meter to a subject's finger positioned within the finger guide. In certain other embodiments, alignment features may be included within the finger guide opening and on the coupling feature to ensure that the glucose meter coupler and finger guide are desirably aligned during use.

In operation, the blood glucose testing system may be used in some embodiments by providing a standard glucose meter, replacing the battery cover of the meter with the glucose meter coupler, and inserting a test strip in the test strip receptacle of the meter. Thereafter, the finger guide may be secured to a subject's finger, and the finger may then be pricked by inserting a lancing device into the finger guide opening of the finger guide sleeve. After removing the lancing device, the coupling feature of the glucose meter coupler may be pressed into the finger guide opening, thereby enabling the test strip to contact a blood droplet left behind after removal of the lancing device and further enabling the meter to calculate and display a blood glucose level.

BRIEF DESCRIPTION OF THE DRAWINGS

Figure 1:
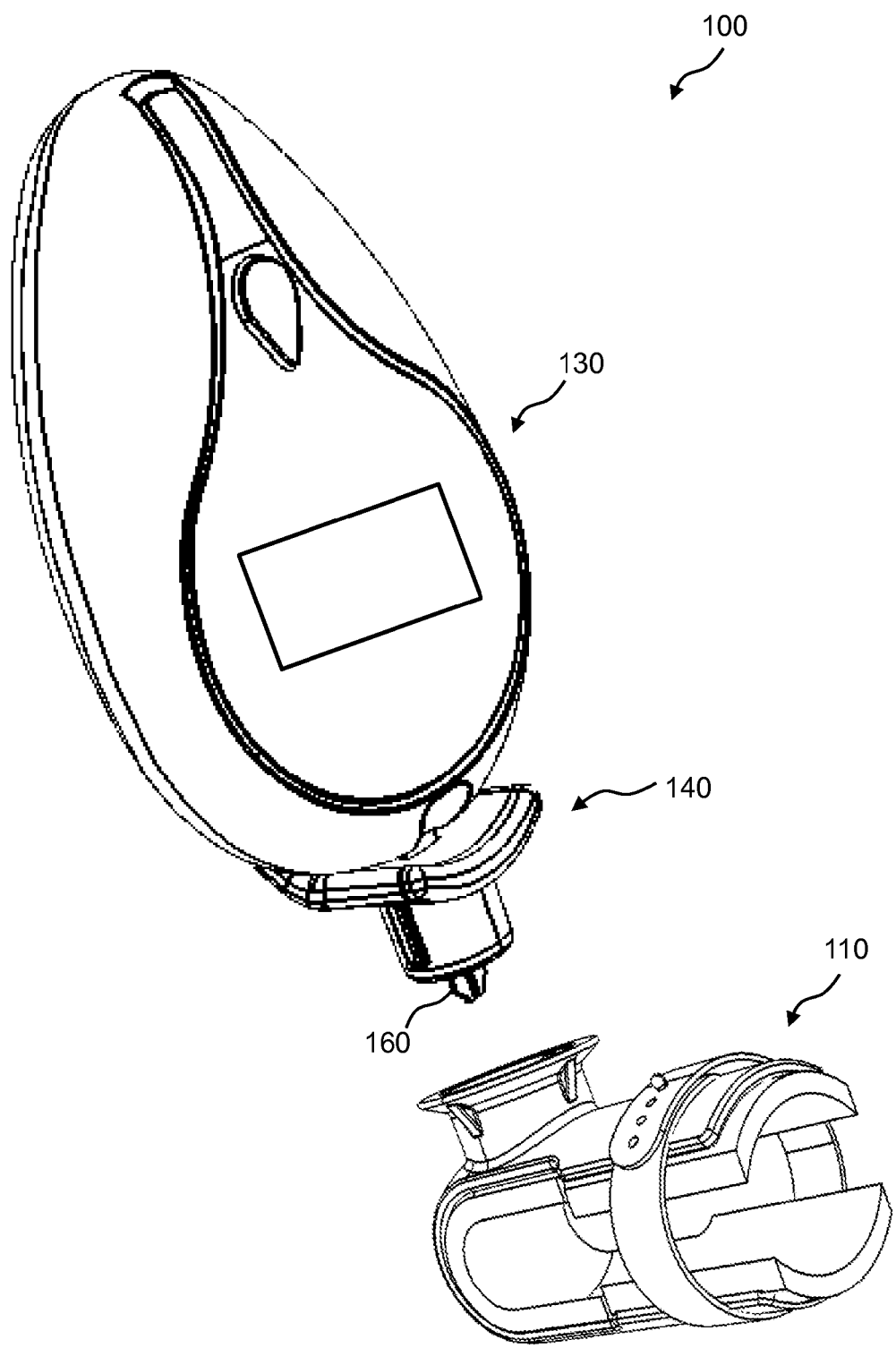
Figure 2:
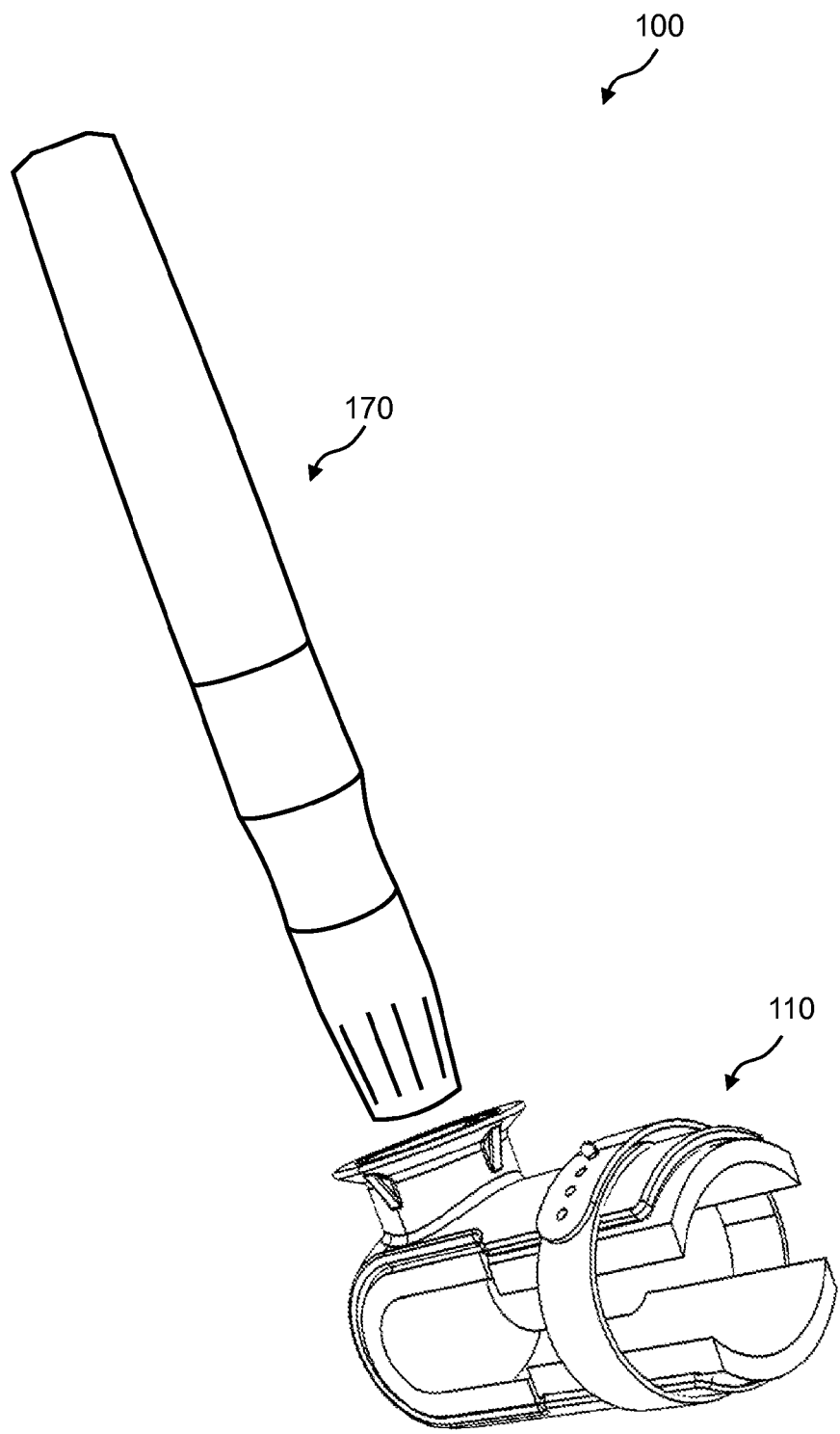
Figure 3:
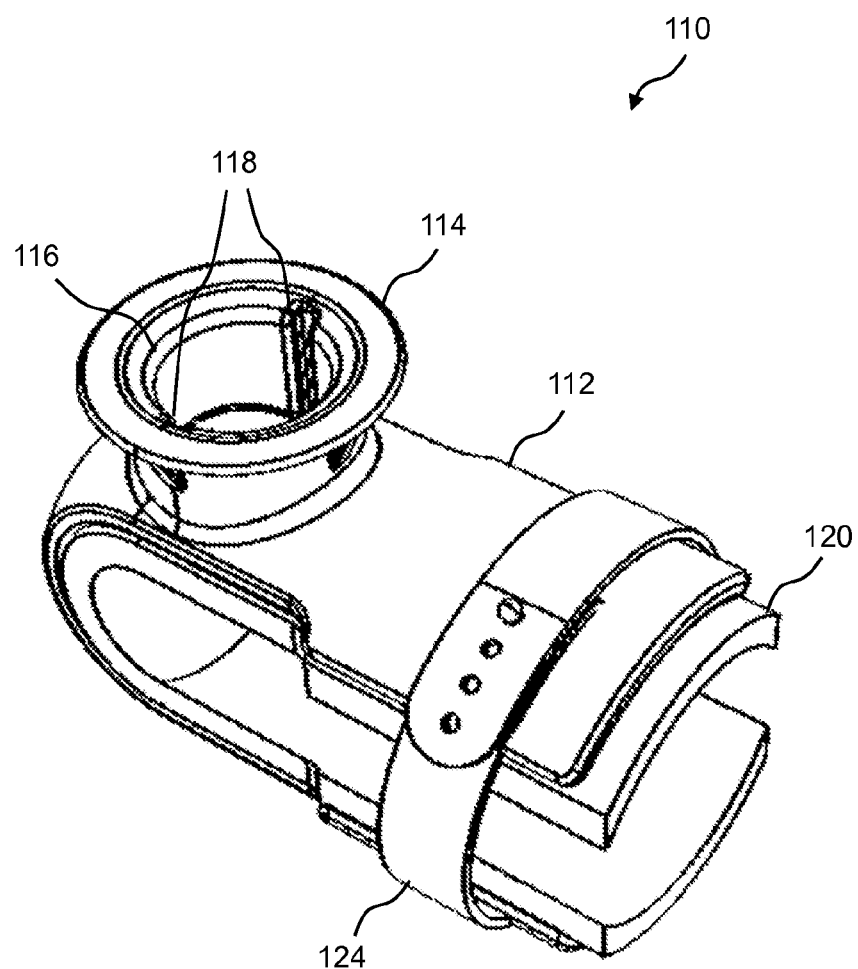
Figure 4:
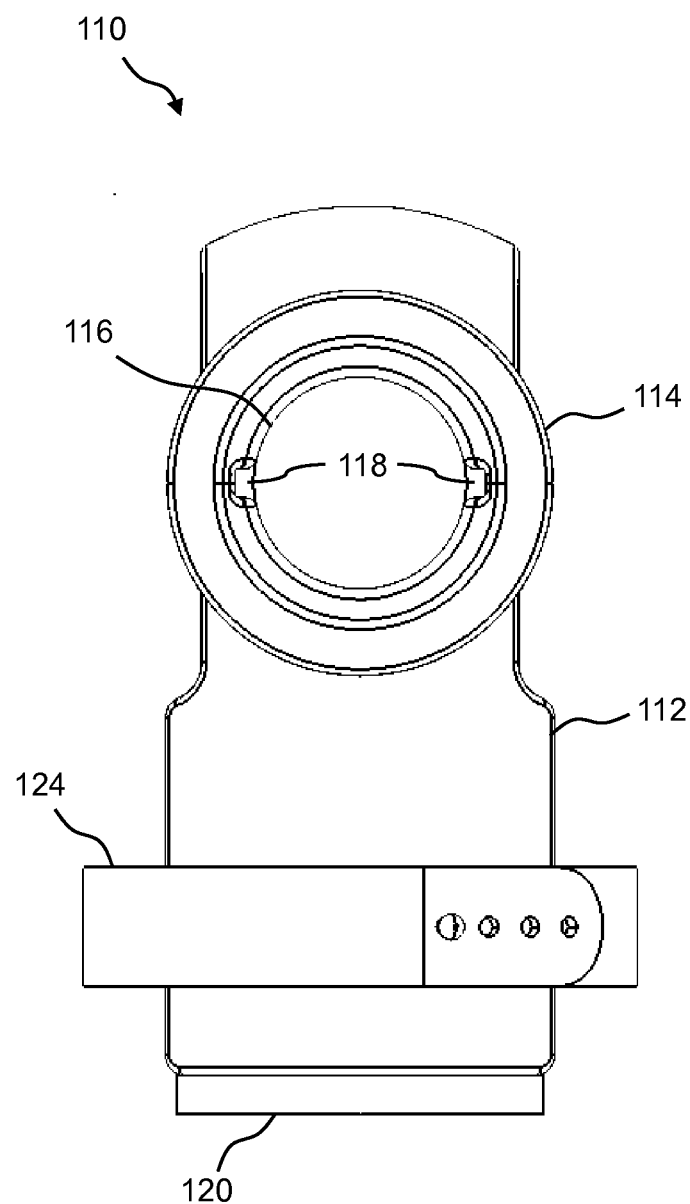
Figure 5A:
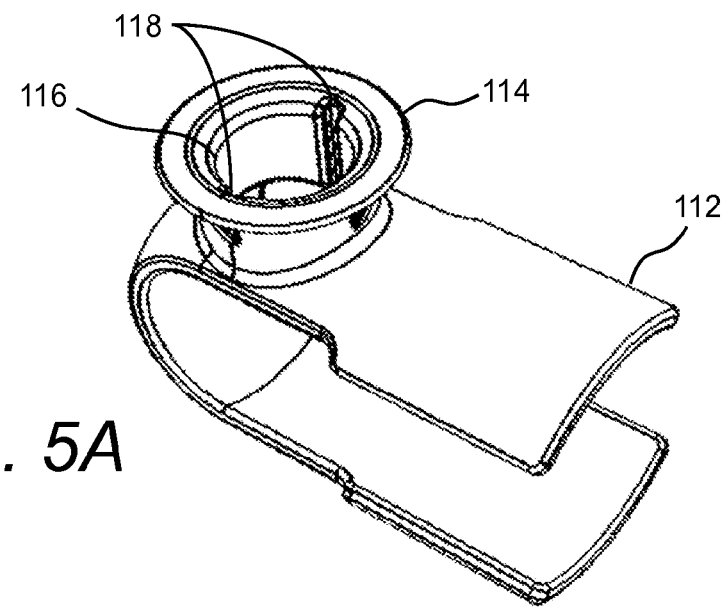
Figure 5B:
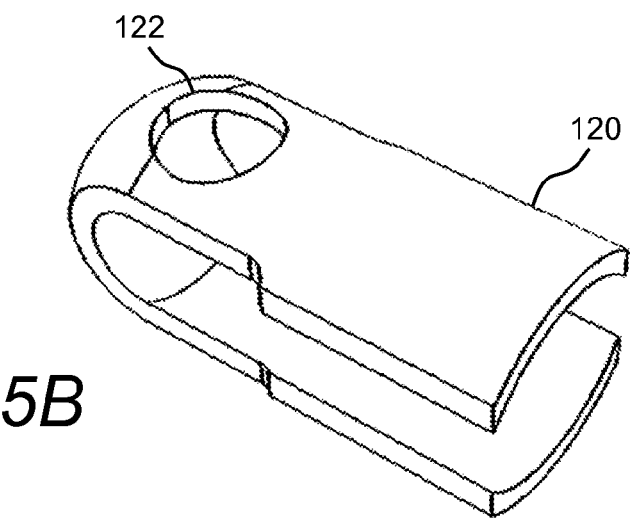
Figure 5C:
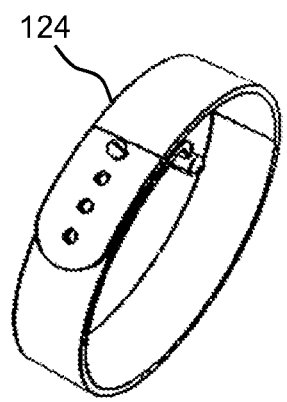
Figure 6:
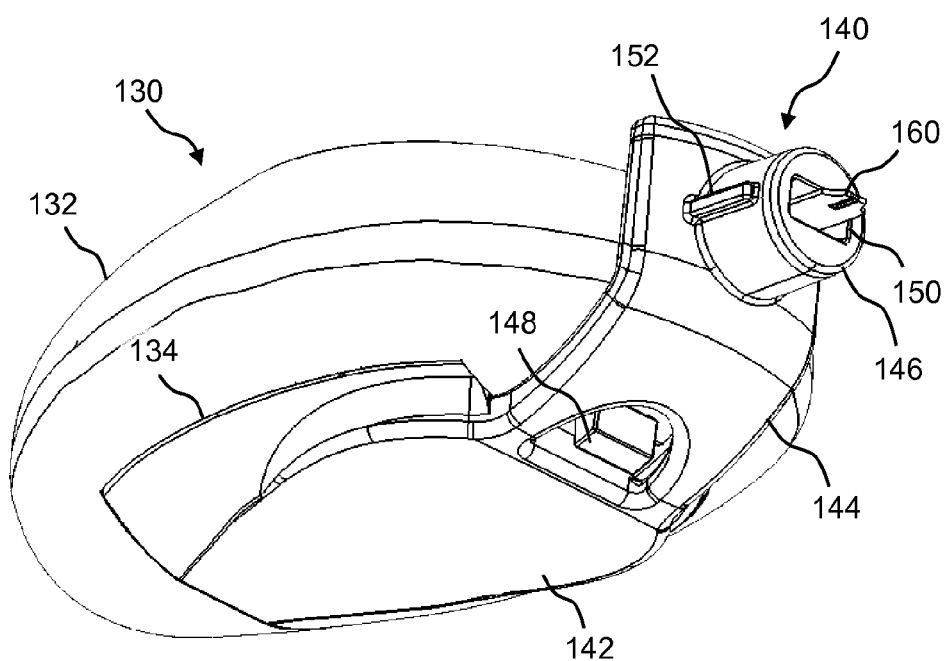
Figure 7:
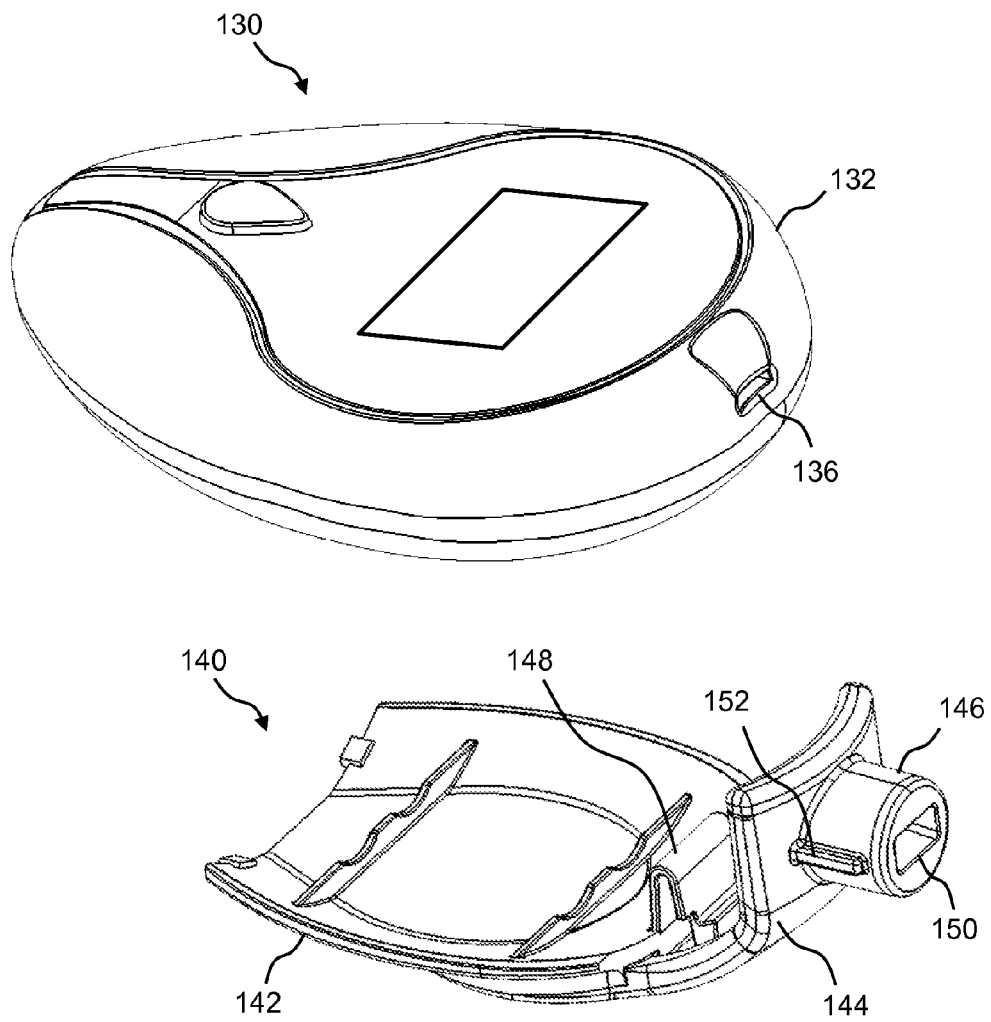
Figure 8:
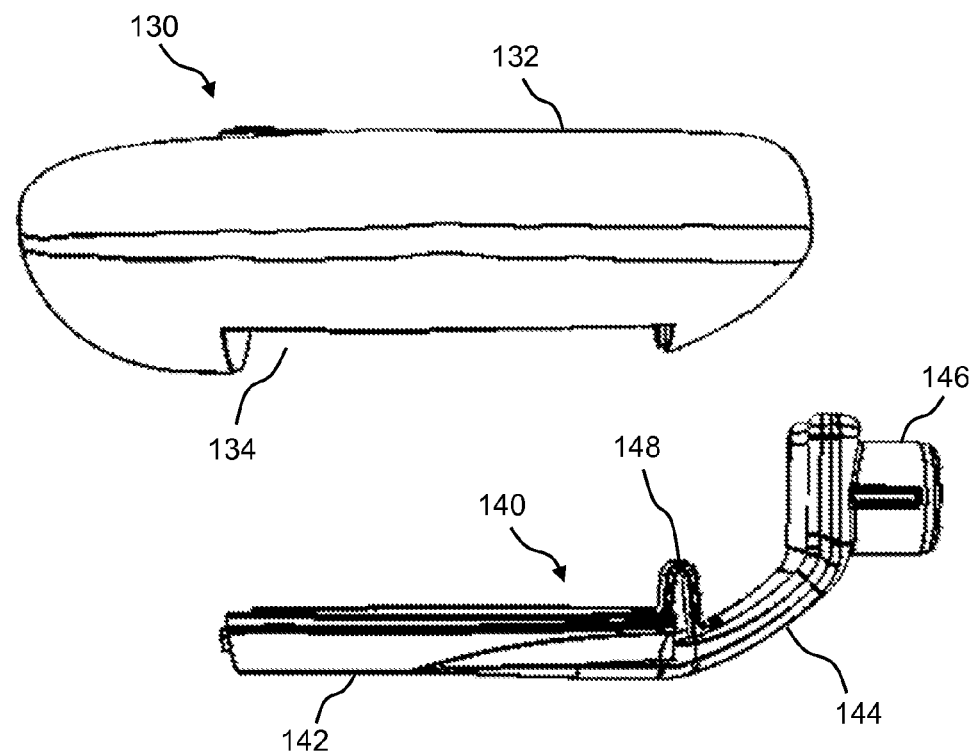
Figure 9:
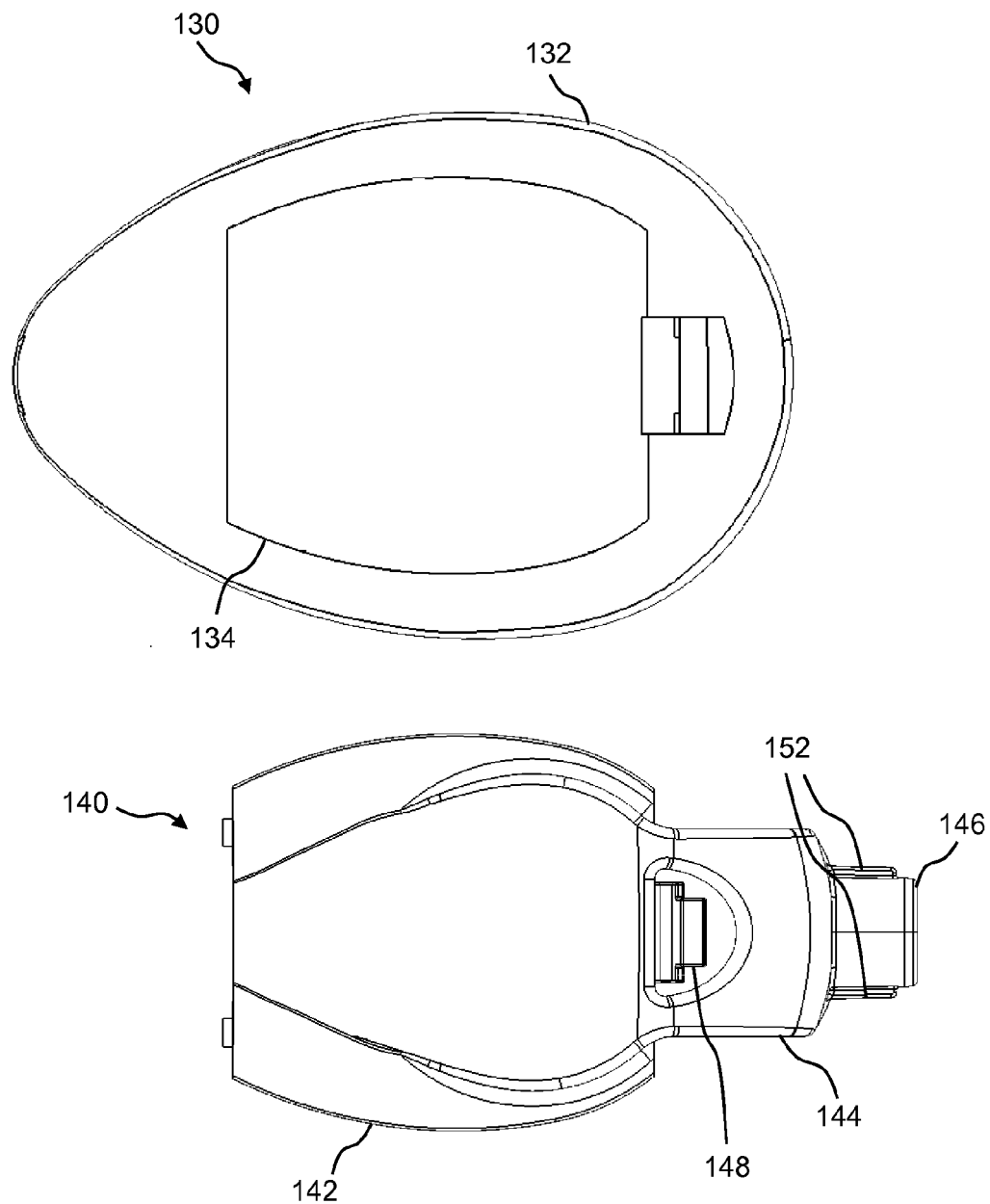
Figure 10:
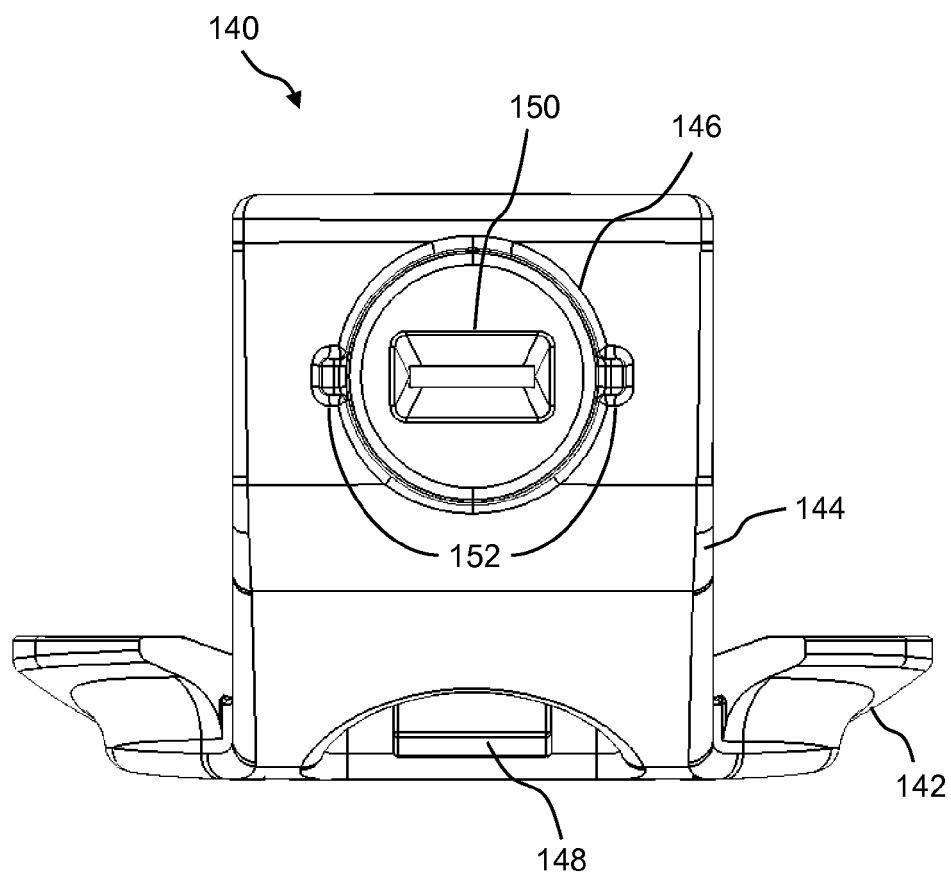
Figure 11:
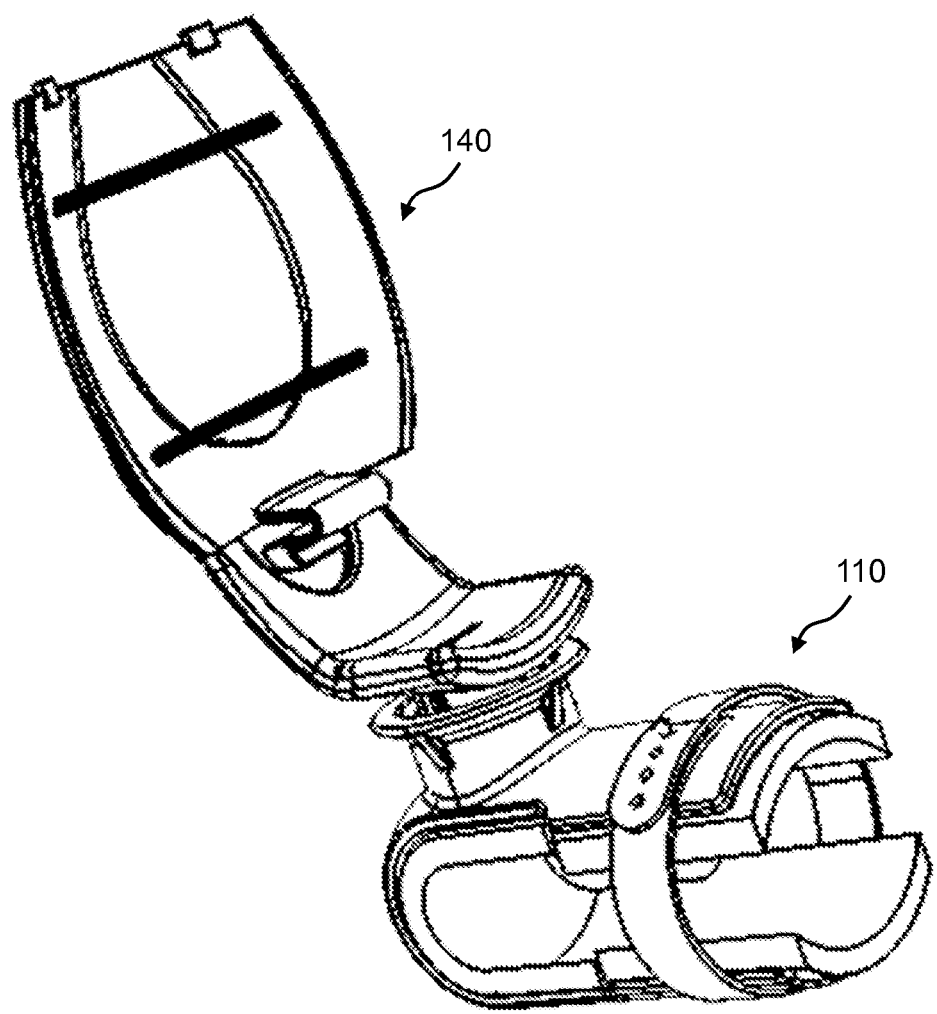
Figure 12:
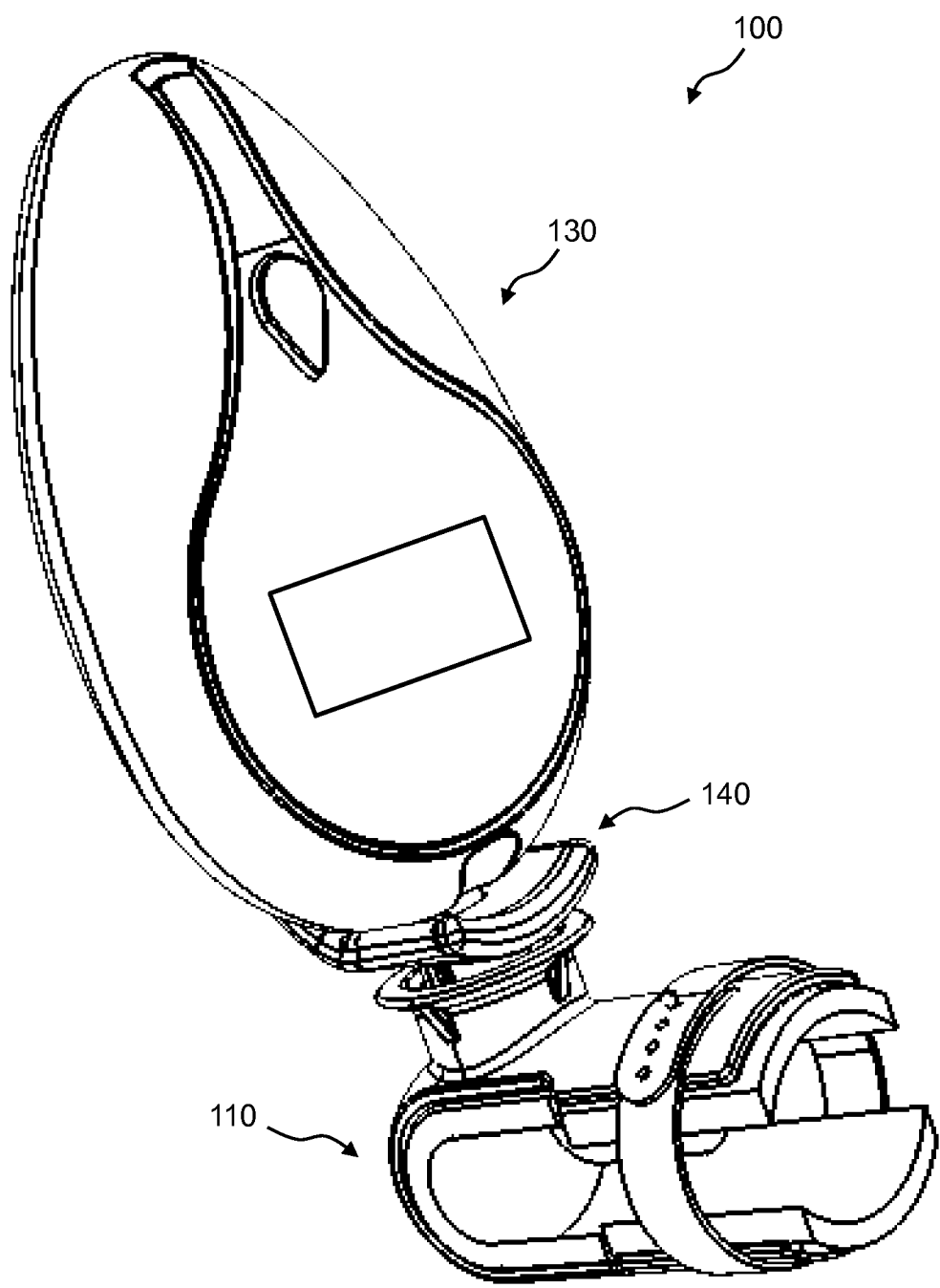
Figure 13:
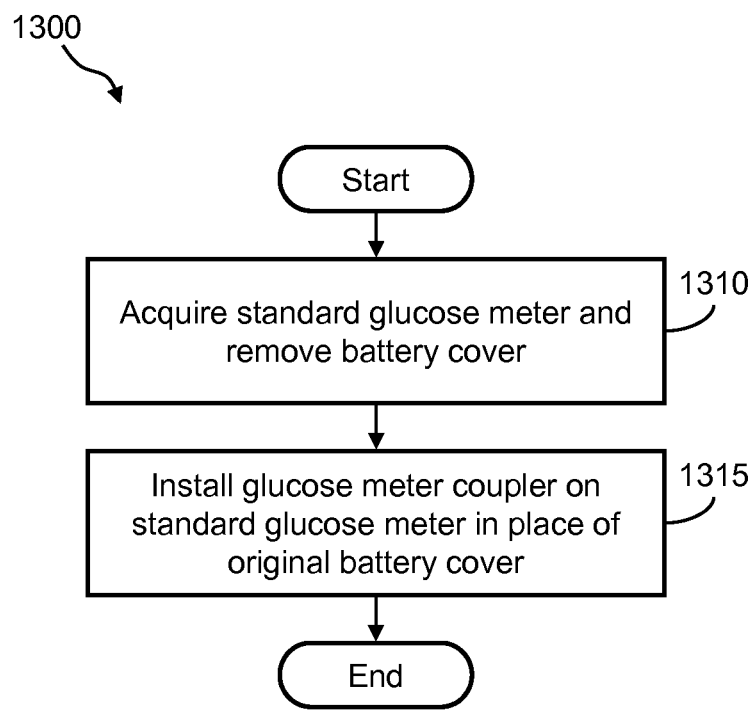
Figure 14:
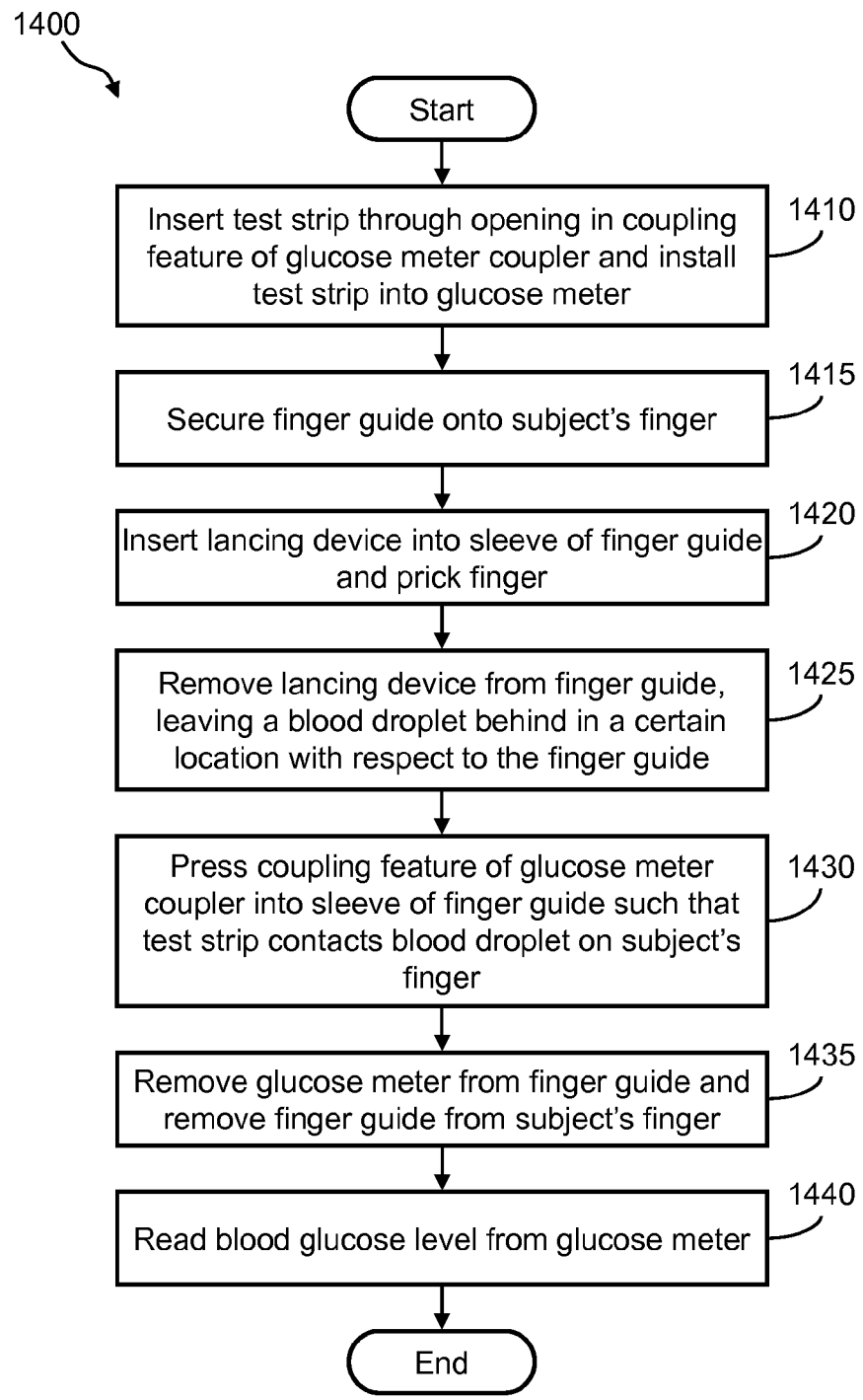
Figure 15:
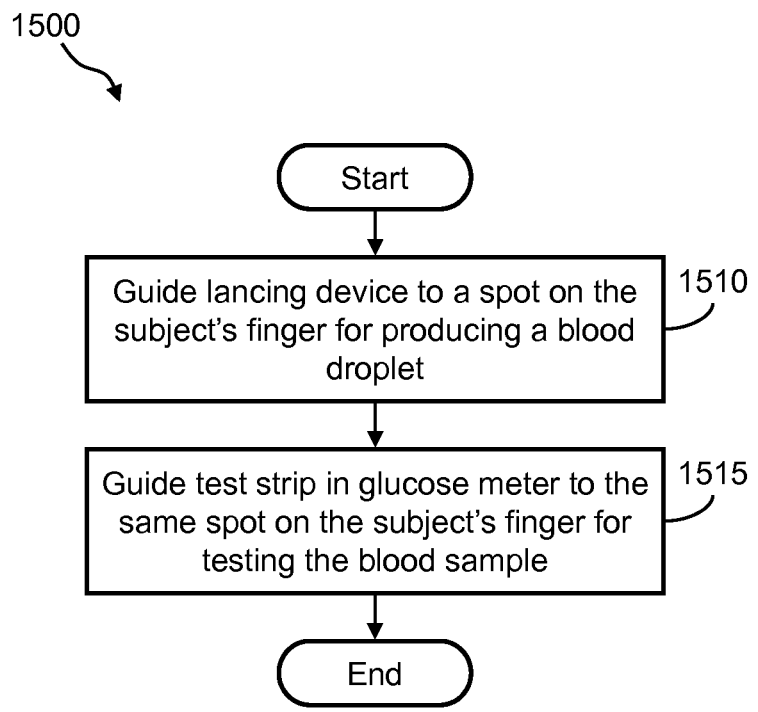

Having thus described the presently disclosed subject matter in general terms, reference will now be made to the accompanying Drawings, which are not necessarily drawn to scale, and wherein:

FIG. 1 and FIG. 2 illustrate perspective views of an example of a blood glucose testing system for ensuring a successful blood glucose test for those individuals who might otherwise have difficulty performing a blood glucose test;

FIG. 3 and FIG. 4 illustrate a perspective view and a top view, respectively, of the finger guide of FIG. 1 and FIG. 2 for assisting the blood glucose test;

FIG. 5A, FIG. 5B, and FIG. 5C illustrate perspective views of three components, respectively, of the finger guide of FIG. 1 and FIG. 2;

FIG. 6 illustrates a perspective view of an example of a glucose meter that has been retrofitted with a glucose meter coupler for assisting the subject of the blood glucose test;

FIG. 7 illustrates perspective views of the glucose meter and the glucose meter coupler when separated;

FIG. 8 illustrates side views of the glucose meter and the glucose meter coupler when separated;

FIG. 9 illustrates bottom views of the glucose meter and the glucose meter coupler when separated;

FIG. 10 illustrates an end view of the glucose meter coupler;

FIG. 11 illustrates a perspective view of the finger guide and the glucose meter coupler when assembled together;

FIG. 12 illustrates a perspective view of the finger guide, the glucose meter, and the glucose meter coupler when assembled together;

FIG. 13 illustrates a flow diagram of an example of a method of retrofitting the glucose meter with the glucose meter coupler;

FIG. 14 illustrates a flow diagram of an example of a method of using the blood glucose testing system; and FIG. 15 illustrates a flow diagram of an example of a method of operating the blood glucose testing system according to a simplest configuration.

DETAILED DESCRIPTION

The presently disclosed subject matter now will be described more fully hereinafter with reference to the accompanying Drawings, in which some, but not all embodiments of the presently disclosed subject matter are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

A blood glucose test system and associated methods are disclosed. More particularly, a blood glucose testing system is provided that includes a finger guide that is wearable by the subject of the blood glucose test and a glucose meter that is retrofitted with a glucose meter coupler. In the blood glucose testing system, the finger guide and the glucose meter coupler on the glucose meter may provide mechanisms for (1) guiding the lancing device to a spot on the subject's finger for producing a blood droplet, and (2) guiding the test strip in the glucose meter to the same spot on the subject's finger for collecting the blood sample. Accordingly, an aspect of the blood glucose testing system disclosed herein is that it includes mechanisms for ensuring a successful blood glucose test for such individuals who include, but are not limited to, those having visual impairment, neurological disorders, and/or tremors, who might otherwise have difficulty performing the steps of a blood glucose test using conventional methods.

FIG. 1 and FIG. 2 illustrate perspective views of an example of a blood glucose testing system 100 for ensuring a successful blood glucose test for those individuals who might otherwise have difficulty performing a blood glucose test. Referring now to FIG. 1, blood glucose testing system 100 includes a finger guide 110 that may be wearable by the subject of the blood glucose test and a glucose meter 130 that may be retrofitted with a glucose meter coupler 140. FIG. 1 also shows a test strip 160 installed in glucose meter 130 and protruding from glucose meter coupler 140. Glucose meter 130 can be any conventional portable glucose meter. Test strip 160 can be any test strip that is commonly used in blood glucose testing operations and is compatible with glucose meter 130.

Referring now to FIG. 2, blood glucose testing system 100 may further include a lancing device 170 that may also be fitted into finger guide 110, which is the same finger guide 110 shown in FIG. 1. Lancing device 170 may be any conventional lancing device or lancet. Finger guide 110 may be implemented using any design that enables the finger guide 110 to be secured to the finger, including a finger splint type of design. Further, finger guide 110 may include a sleeve, wherein the sleeve has an opening that may be used to (1) guide lancing device 170 to a spot on the subject's finger for producing a blood droplet, and (2) guide test strip 160 that is protruding from glucose meter coupler 140 to the same spot on the subject's finger for collecting the blood sample. More details of finger guide 110 are shown and described with reference to FIGS. 3, 4, 5A, 5B, and 5C. More details of glucose meter coupler 140 are shown and described with reference to FIGS. 6, 7, 8, 9, and 10.

FIG. 3 and FIG. 4 illustrate a perspective view and a top view, respectively, of an example of finger guide 110 for assisting the blood glucose test. In some embodiments, finger guide 110 includes a finger guide body 112 that is configured to be fit onto a finger and tightened in a finger splint type of fashion. For example, one end of finger guide body 112 may be open so that finger guide 110 may be slipped onto the tip of the subject's finger. A finger guide sleeve 114 having an opening 116 may also be provided at one end of finger guide body 112, positioned to expose a desired are of skin for lancing and testing. Opening 116 of finger guide sleeve 114 provides an opening in finger guide body 112 through which a lancing device, such as lancing device 170, and/or a test strip, such as test strip 160, may be inserted during the blood glucose test. Accordingly, the diameter of opening 116 of finger guide sleeve 114 may be selected to substantially correspond to standard lancing devices or lancets so that finger guide sleeve 114 can provide a suitable guide for pricking the finger of the subject of the blood glucose test.

In one embodiment, two alignment slots 118 are may be provided along the walls of opening 116 of finger guide sleeve 114. In certain other embodiments, however, finger guide sleeve 114 is not limited to two alignment slots 118, as this is exemplary only. Finger guide sleeve 114 may include any number of alignment slots 118 as may be advantageously desired.

In some embodiments, the inside of finger guide body 112 may be lined with finger guide padding 120 for providing comfort to the wearer of finger guide 110. Finger guide padding 120 can be formed, for example, of foam, rubber, or any other compliant material. In some embodiments, the finger guide padding 120 is about 3-5 mils thick, but finger guide padding may be of any thickness desirable. Finger guide padding 120 may also include an opening (see FIG. 5B) that substantially corresponds to the location of finger guide sleeve 114 and opening 116 of finger guide body 112. Finger guide 110 may also include a finger guide strap 124 that wraps around finger guide body 112 and finger guide padding 120. Finger guide strap 124 may be adjustable so that finger guide 110 may be comfortably secured to the subject's finger. In one embodiment, finger guide strap 124 is a cloth or nylon strap with Velcro® as the securing mechanism. In certain other embodiments, finger guide strap 124 may be secured by any other adjustable securing means.

Referring now to FIG. 5A, FIG. 5B, and FIG. 5C, perspective views of three components of finger guide 110 of FIG. 3, respectfully, are provided. Namely, FIG. 5A shows finger guide body 112, FIG. 5B shows finger guide padding 120, and FIG. 5C shows finger guide strap 124. Referring to FIG. 5A, the finger guide body 112, which includes finger guide sleeve 114, may be formed of any desirable material. In one example, finger guide body 112, which includes finger guide sleeve 114, is formed of plastic using a standard injection molding process. Referring now to FIG. 5B, finger guide padding 120 is depicted. Finger guide padding 120 may include, for example, an opening 122 that may correspond to the location of finger guide sleeve 114 of finger guide body 112.

Referring now to FIG. 6, FIG. 7, FIG. 8, FIG. 9, and FIG. 10, various views of glucose meter coupler 140 in relation to glucose meter 130 are provided. Namely, FIG. 6 shows a perspective view of an example of glucose meter 130 that has been retrofitted with glucose meter coupler 140 for assisting the subject of the blood glucose test. In particular, FIG. 6 shows the battery cover-side of glucose meter 130. FIG. 7 shows perspective views of glucose meter 130 and glucose meter coupler 140 when separated. FIG. 8 shows side views of glucose meter 130 and glucose meter coupler 140 when separated. FIG. 9 shows bottom views of glucose meter 130 and glucose meter coupler 140 when separated. FIG. 10 shows an end view of glucose meter coupler 140.

Again, glucose meter 130 may be a conventional glucose meter that has standard display and control features. Glucose meter 130 includes, for example, a meter body 132, a battery compartment 134, and a test strip receptacle 136. In certain embodiments of blood glucose testing system 100, glucose meter coupler 140 may be installed in place of the original battery cover (not shown) at battery compartment 134 of glucose meter 130. For example, glucose meter coupler 140 may include a battery cover 142, an arm 144 extending from one end of battery cover 142, a coupling feature 146 at the end of arm 144, and a locking mechanism 148. Glucose meter coupler 140 may be formed of plastic using a standard injection molding process, or any other material as desired.

Battery cover 142 and locking mechanism 148 of glucose meter coupler 140 include substantially the same features as the original battery cover (not shown) of glucose meter 130 so that the battery cover 142 and locking mechanism 148 portion of glucose meter coupler 140 can be fitted and installed at battery compartment 134 of glucose meter 130. For example, locking mechanism 148 may include a locking tab that can be press-fitted with spring force and locked to corresponding features in battery compartment 134 of glucose meter 130.

When glucose meter coupler 140 is installed on glucose meter 130, arm 144 may extend from one end of battery cover 142 toward test strip receptacle 136 of glucose meter 130, while generally following the contour of meter body 132. Additionally, coupling feature 146 may be at the end of arm 144 opposite battery cover 142 and may be substantially aligned with test strip receptacle 136 of glucose meter 130. An opening 150 may also be provided in coupling feature 146, which allows test strip 160 to pass through coupling feature 146 and be fitted into test strip receptacle 136 of glucose meter 130.

In some embodiments, coupling feature 146 may include, for example, two alignment features 152, though any number and/or configuration of alignment features may be included as desired. The size and geometry of coupling feature 146 of glucose meter coupler 140 may be configured to substantially correspond to the size and geometry of opening 116 of finger guide sleeve 114 of finger guide 110. Additionally, the locations, size, and number of alignment features 152 should substantially correspond to the locations, size, and number of alignment slots 118 in finger guide sleeve 114 of finger guide 110. Accordingly, coupling feature 146 of glucose meter coupler 140 is configured to be fitted into and automatically aligned with finger guide sleeve 114 of finger guide 110, as depicted in FIG. 11 and FIG. 12.

FIG. 11 shows a perspective view of certain embodiments of finger guide 110 and glucose meter coupler 140 when assembled together. Similarly, FIG. 12 shows a perspective view of certain embodiments of finger guide 110, glucose meter 130, and glucose meter coupler 140 when assembled together. In certain other embodiments, alignment slots 118 in finger guide sleeve 114 of finger guide 110 and alignment features 152 in coupling feature 146 of glucose meter coupler 140 are omitted. In these embodiments, coupling feature 146 of glucose meter coupler 140 may be press-fitted into finger guide sleeve 114 of finger guide 110 with any rotational orientation and without detriment to the operation of blood glucose testing system 100.

Glucose meter coupler 140 is not limited to the exact implementation shown in FIG. 1 through FIG. 12. This is exemplary only. The features of glucose meter coupler 140 can vary from one brand and/or type of glucose meter to another. Accordingly, the features of glucose meter coupler 140 may be tailored or customized to correspond to the battery compartment and test strip receptacle of any brand and/or type of portable glucose meter. Alternatively, the glucose meter coupler 140 may be tailored or customized to correspond to any other feature of glucose meter 130 that would allow glucose meter coupler 140 to be coupled to glucose meter coupler 140, including but not limited to use of adhesives, clips, or any other comparable coupling means.

The operation of blood glucose testing system 100 can be summarized as follows. With reference to FIG. 1 through FIG. 12, the subject of the blood glucose test and/or a caretaker of the subject of the blood glucose test slides finger guide 110 onto one of the subject's fingers and optionally secures finger guide 110 to the finger using finger guide strap 124. Finger guide 110 is positioned with line of sight through opening 116 of finger guide sleeve 114 to the subject's skin. Subsequently, lancing device 170 is inserted into finger guide sleeve 114 of finger guide 110 (see FIG. 2) and the subject's finger is pricked in order to generate a blood droplet. Lancing device 170 is then removed from finger guide 110. A test strip 160 may then be inserted through opening 150 of coupling feature 146 of glucose meter coupler 140 thereby installing the test strip 160 into test strip receptacle 136 of glucose meter 130, as shown in FIG. 6. Then, coupling feature 146 of glucose meter coupler 140 is press-fitted into finger guide sleeve 114 of finger guide 110, as shown in FIG. 12. Thereby coming into contact with the previously generated blood sample and allowing for a reading of the subject's blood sugar level to be generated and displayed on glucose meter 130.

FIG. 13 illustrates a flow diagram of an example of a method 1300 of retrofitting glucose meter 130 with glucose meter coupler 140. Method 1300 may include, but is not limited to, the following steps.

At a step 1310, a standard glucose meter is provided and the battery cover is removed. For example, glucose meter 130 is provided and its original equipment battery cover at battery compartment 134 is removed, as shown in FIG. 8.

At a step 1315, a glucose meter coupler 140 with features that substantially correspond to the features of the original battery cover of the standard glucose meter is provided. Then, the glucose meter coupler 140 is installed on the standard glucose meter in place of its original battery cover. For example, the battery cover 142 and locking mechanism 148—portion of glucose meter coupler 140 is installed at battery compartment 134 of glucose meter 130, as shown in FIG. 6.

FIG. 14 illustrates a flow diagram of an example of a method 1400 of using blood glucose testing system 100. Method 1400 may include, but is not limited to, the following steps.

At a step 1410, test strip 160 is inserted through opening 150 in coupling feature 146 of glucose meter coupler 140 and test strip 160 is installed into test strip receptacle 136 of glucose meter 130.

At a step 1415, finger guide 110 is secured onto the subject's finger. For example, the subject of the blood glucose test and/or a caretaker of the subject of the blood glucose test slides finger guide 110 onto the subject's finger and secures finger guide 110 using finger guide strap 124. Finger guide 110 is positioned with line of sight to the subject's skin through opening 116 of finger guide sleeve 114.

At a step 1420, lancing device 170 is inserted into finger guide 110 and the subject's finger is pricked. For example, lancing device 170 is inserted into opening 116 of finger guide sleeve 114 of finger guide 110 and the subject's finger is pricked in order to generate a blood droplet.

At a step 1425, lancing device 170 is removed from finger guide 110, leaving a blood droplet behind. Namely, lancing device 170 is removed from opening 116 of finger guide sleeve 114 of finger guide 110. A blood droplet is left behind on the subject's finger. The blood droplet is in a certain location with respect to finger guide sleeve 114 of finger guide 110.

At a step 1430, coupling feature 146 of glucose meter coupler 140 is press-fitted into finger guide sleeve 114 of finger guide 110 such that test strip 160 contacts blood droplet on subject's finger. Namely, because the blood droplet that was created using lancing device 170 in step 1425 is in a certain location with respect to finger guide sleeve 114, the test strip 160 protruding from coupling feature 146 will contact the same location on subject's finger because it is guided by the same finger guide sleeve 114.

At a step 1435, glucose meter coupler 140 of glucose meter 130 is removed from finger guide sleeve 114 of finger guide 110. Then, finger guide 110 is removed from the subject's finger.

At a step 1440, the blood glucose level is read from the display of glucose meter 130.

FIG. 15 illustrates a flow diagram of an example of a method 1500 of operating blood glucose testing system 100 according to a simplest configuration. Method 1500 may include, but is not limited to, the following steps.

At a step 1510, the lancing device is guided to a spot on the subject's finger for producing a blood droplet. For example, by inserting lancing device 170 into finger guide sleeve 114 of finger guide 110, lancing device 170 is guided to a spot on the subject's finger for producing a blood droplet.

At a step 1515, the test strip in the glucose meter is guided to the same spot on the subject's finger for collecting the blood sample. For example, by inserting coupling feature 146 of glucose meter coupler 140 into finger guide sleeve 114 of finger guide 110, test strip 160, which is protruding from coupling feature 146, is guided to the same spot on the subject's finger to which the lancing device 170 was guided in step 1510, and the blood sample is tested.

In summary, blood glucose testing system 100 and methods 1300, 1400, and 1500 may be used to guide a lancing device, such as lancing device 170, to a spot on the subject's finger for producing a blood droplet, and subsequently guide a test strip, such as test strip 160, in a glucose meter, such as glucose meter 130, to the same spot on the subject's finger for collecting the blood sample. Accordingly, blood glucose testing system 100 and methods 1300, 1400, and 1500 may be used to ensure a successful blood glucose test for any individual, but in particular those who might otherwise have difficulty performing the steps of the blood glucose test, such as, but not limited to, those individuals having visual impairment, neurological disorders, and/or tremors.

The subject treated by the presently disclosed methods in their many embodiments is desirably a human subject, although it is to be understood that the methods described herein are effective with respect to all vertebrate species, which are intended to be included in the term "subject."

A "subject" can include a human subject for medical purposes, such as for the treatment of an existing condition or disease or the prophylactic treatment for preventing the onset of a condition or disease, or an animal subject for medical, veterinary purposes, or developmental purposes. Suitable animal subjects include mammals including, but not limited to, primates, e.g., humans, monkeys, apes, and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a condition or disease. Thus, the terms "subject" and "patient" are used interchangeably herein.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, parameters, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

Although the foregoing subject matter has been described in some detail by way of illustration and example for purposes of clarity of understanding, it will be understood by those skilled in the art that certain changes and modifications can be practiced within the scope of the appended claims.

That which is claimed:
1. A blood glucose testing system, comprising:
a finger guide, wherein the finger guide comprises:

a finger guide body;
a finger guide sleeve;
a finger guide strap; and
a finger guide opening disposed within the finger guide sleeve; and
a glucose meter coupler, wherein the glucose meter coupler comprises:
a locking mechanism configured to attach the glucose meter coupler to a glucose meter, and
a coupling feature configured to couple a glucose meter and the glucose meter coupler installed thereon to the finger guide via the finger guide opening, wherein the coupling feature further comprises a test strip opening configured to allow a test strip to pass from the glucose meter to a finger positioned within the finger guide.

2. The blood glucose testing system of claim 1, wherein the finger guide is secured to the finger in a splint-like manner.

3. The blood glucose testing system of claim 1, wherein the finger guide strap further comprises a securing mechanism.

4. The blood glucose testing system of claim 3, wherein the securing mechanism is Velcro®.

5. The blood glucose testing system of claim 1, wherein the finger guide further comprises finger guide padding.

6. The blood glucose testing system of claim 5, wherein the finger guide padding further comprises a finger guide padding opening having dimensions substantially similar to the finger guide opening.

7. The blood glucose testing system of claim 5, wherein the finger guide padding is comprised of foam.

8. The blood glucose testing system of claim 5, wherein the finger guide padding is comprised of rubber.

9. The blood glucose testing system of claim 1, wherein the finger guide opening is further configured to receive a lancing device.

10. The blood glucose testing system of claim 1, wherein the finger guide body is comprised of plastic.

11. A blood glucose testing system comprising:
a finger guide, wherein the finger guide comprises:
a finger guide body;
a finger guide sleeve; and
a finger guide opening disposed within the finger guide sleeve; and
a glucose meter coupler, wherein the glucose meter coupler comprises:
a locking mechanism configured to attach the glucose meter coupler to a glucose meter, and
a coupling feature configured to couple a glucose meter and the glucose meter coupler installed thereon to the finger guide via the finger guide opening, wherein the coupling feature further comprises a test strip opening configured to allow a test strip to pass from the glucose meter to a finger positioned within the finger guide, wherein the glucose meter coupler comprises a battery cover portion configured to replace a battery cover of the glucose meter.

12. The blood glucose testing system of claim 11, wherein the locking mechanism comprises a locking tab configured to operatively clip into corresponding features in a battery compartment of the glucose meter.

13. The blood glucose testing system of claim 12, wherein the locking tab is configured to be unclipped from the corresponding features of the battery compartment to facilitate removal of the glucose meter coupler from the glucose meter.

14. The blood glucose testing system of claim 11, wherein the glucose meter coupler further comprises an arm connecting the battery cover portion to the coupling feature.

15. A blood glucose testing system, comprising:
a finger guide, wherein the finger guide comprises:
a finger guide body;
a finger guide sleeve; and
a finger guide opening disposed within the finger guide sleeve; and
a glucose meter coupler, wherein the glucose meter coupler comprises:
a locking mechanism configured to attach the glucose meter coupler to a glucose meter, and
a coupling feature configured to couple a glucose meter and the glucose meter coupler installed thereon to the finger guide via the finger guide opening, wherein the coupling feature further comprises a test strip opening configured to allow a test strip to pass from the glucose meter to a finger positioned within the finger guide,
wherein the system further comprises alignment features disposed on the finger guide sleeve and the coupling feature, wherein the alignment features of the coupling feature, thereby enabling consistent orientation of the finger guide relative to the glucose meter coupler when coupled together, and
wherein the alignment features of the finger guide sleeve comprise alignment slots configured to receive corresponding raised alignment features disposed on an outer perimeter of the coupling feature.

16. The blood glucose testing system of claim 15 wherein the finger guide sleeve comprises two alignment slots and the outer perimeter of the coupling feature comprises two corresponding raised features.

17. A method of using a blood glucose testing system comprising the steps of:
a) providing a standard glucose meter, wherein the glucose meter comprises a battery compartment, a battery cover, and a test strip receptacle;
b) removing the battery cover;
c) providing a glucose meter coupler and installing the glucose meter coupler on the glucose meter in place of the battery cover, wherein the glucose meter coupler comprises a coupling feature;
d) inserting a test strip through a test strip opening of the coupling feature and into the test strip receptacle;
e) providing a finger guide, wherein the finger guide comprises a finger guide body, a finger guide sleeve, and a finger guide opening disposed within the finger guide sleeve;
f) securing the finger guide to a subject's finger;
g) inserting a lancing device into the finger guide opening and pricking the subject's finger;
h) removing the lancing device from the finger guide, leaving a blood droplet behind in a desired location relative to the finger guide;
i) pressing the coupling feature of the glucose meter coupler into the finger guide opening such that the test strip contacts the blood droplet on the subject's finger, thereby enabling the glucose meter to compute a blood glucose level;
j) removing the glucose meter coupler and attached glucose meter from the finger guide;
k) removing the finger guide from the subject's finger; and
l) reading the blood glucose level from a display on the glucose meter.

18. The method of claim 17, wherein the finger guide sleeve and the coupling feature of the glucose meter coupler further comprise alignment features that ensure the finger guide is desirably aligned relative to the glucose meter coupler when coupled together.

* * * * *